(12) United States Patent
Ceccarelli et al.

(10) Patent No.: US 9,315,502 B2
(45) Date of Patent: Apr. 19, 2016

(54) IMIDAZOPYRIDINE DERIVATIVES

(71) Applicant: Hoffmann-La Roche Inc., Little Falls, NJ (US)

(72) Inventors: Simona M. Ceccarelli, Basel (CH); Ravi Jagasia, Loerrach (DE); Roland Jakob-Roetne, Inzlingen (DE); Juergen Wichmann, Steinen (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 14/723,061

(22) Filed: May 27, 2015

(65) Prior Publication Data

US 2015/0259341 A1     Sep. 17, 2015

Related U.S. Application Data

(63) Continuation of application No. PCT/EP2013/074662, filed on Nov. 26, 2013.

(30) Foreign Application Priority Data

Nov. 29, 2012  (EP) ..................... 12194721

(51) Int. Cl.
| | |
|---|---|
| C07D 401/02 | (2006.01) |
| C07D 401/10 | (2006.01) |
| A61K 31/437 | (2006.01) |
| A61K 31/4353 | (2006.01) |
| C07D 471/04 | (2006.01) |

(52) U.S. Cl.
CPC .................. C07D 471/04 (2013.01)

(58) Field of Classification Search
CPC .. C07D 401/02; C07D 401/10; A61K 31/437; A61K 31/4353
USPC .......................... 546/121; 514/300
See application file for complete search history.

(56) References Cited

U.S. PATENT DOCUMENTS

2008/0255358 A1* 10/2008 Bamford .............. C07D 471/04
                                                            544/333

FOREIGN PATENT DOCUMENTS

| WO | 02/02557 A2 | 1/2002 |
|---|---|---|
| WO | 2007/082806 A1 | 7/2007 |

* cited by examiner

*Primary Examiner* — Niloofar Rahmani
(74) *Attorney, Agent, or Firm* — Brian L. Buckwalter

(57) ABSTRACT

The present invention relates to compounds of general formula

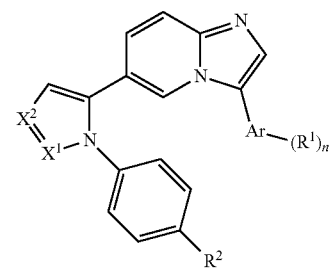

wherein
Ar is phenyl or pyridinyl;
$X^1$ is N or CH,
$X^2$ is N or CH, with the proviso that only one of $X^1$ or $X^2$ is N and the other is CH;
$R^1$ is hydrogen, halogen, lower alkyl, lower alkoxy, lower alkyl substituted by halogen, cyano or $S(O)_2$-lower alkyl;
$R^2$ is hydrogen, halogen, lower alkyl, lower alkoxy, lower alkyl substituted by halogen or cyano;
n is 1 or 2;
or to a pharmaceutically acceptable acid addition salt, to a racemic mixture or to its corresponding enantiomer and/or optical isomers thereof.

The compounds may be used for the treatment of schizophrenia, obsessive-compulsive personality disorder, major depression, bipolar disorders, anxiety disorders, normal aging, epilepsy, retinal degeneration, traumatic brain injury, spinal cord injury, post-traumatic stress disorder, panic disorder, Parkinson's disease, dementia, Alzheimer's disease, mild cognitive impairment, chemotherapy-induced cognitive dysfunction, Down syndrome, autism spectrum disorders, hearing loss, tinnitus, spinocerebellar ataxia, amyotrophic lateral sclerosis, multiple sclerosis, Huntington's disease, stroke, radiation therapy, chronic stress, abuse of neuro-active drugs, such as alcohol, opiates, methamphetamine, phencyclidine and cocaine.

10 Claims, No Drawings

IMIDAZOPYRIDINE DERIVATIVES

The present invention relates to compounds of general formula

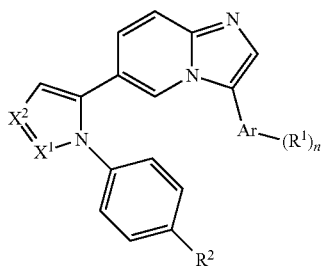

wherein
Ar is phenyl or pyridinyl;
$X^1$ is N or CH,
$X^2$ is N or CH, with the proviso that only one of $X^1$ or $X^2$ is N and the other is CH;
$R^1$ is hydrogen, halogen, lower alkyl, lower alkoxy, lower alkyl substituted by halogen, cyano or $S(O)_2$-lower alkyl;
$R^2$ is hydrogen, halogen, lower alkyl, lower alkoxy, lower alkyl substituted by halogen or cyano;
n is 1 or 2;
or to a pharmaceutically acceptable acid addition salt, to a racemic mixture or to its corresponding enantiomer and/or optical isomers thereof.

Now it has been shown that the present compounds stimulate neurogenesis from neural stem cells (NSCs). Neurogenesis occurs in the developing and adult brain. Conceptually, this process of neurogenesis can be divided into four steps: (i) proliferation of NSCs; (ii) neuronal fate determination of NSC; (iii) survival and maturation of new neurons; and (iv) functional integration of new neurons into the neuronal network.

Adult neurogenesis is a developmental process that occurs throughout live in the adult brain whereby new functional neurons are generated from adult neural stem cells. Constitutive adult neurogenesis under physiological conditions occurs mainly in two "neurogenic" brain regions, 1) the sub-granular zone (SGZ) in the dentate gyrus of the hippocampus, where new dentate granule cells are generated, 2) the sub-ventricular zone (SVZ) of the lateral ventricles, where new neurons are generated and then migrate through the rostral migratory stream (RMS) to the olfactory bulb to become interneurons.

Extensive evidence suggests that hippocampal adult neurogenesis plays an important role in cognitive and emotional states albeit the precise function remains elusive. It has been argued that the relatively small number of newborn granule neurons can affect global brain function because they inner-vate many interneurons within the dentate gyrus, each of which inhibits hundreds of mature granule cells leading to a neurogenesis-dependent feedback inhibition. In combination with a low threshold for firing the newborn neurons trigger responses to very subtle changes in context. Disturbances in this process may manifest behaviorally in deficits in pattern separation related to psychiatric diseases. For example, adult hippocampal neurogenesis correlates with cognitive and emotional capacity, e.g. physical exercise, exposure to an enriched environment and typical antidepressants concomitantly promote adult hippocampal neurogenesis and cognition and/or emotional states, while chronic stress, depression, sleep deprivation and aging decrease adult neurogenesis and associate with negative cognitive and/or emotional states (Neuron 70, May 26, 2011, pp 582-588 and pp 687-702; WO 2008/046072). Interestingly, antidepressants promote hippocampal adult neurogenesis and their effects on certain behaviors require the stimulation of neurogenesis. Neurogenesis in other adult CNS regions is generally believed to be very limited under normal physiological conditions, but could be induced after injury such as stroke, and central and peripheral brain damage.

It is therefore believed that stimulation of adult neurogenesis represents a neuro-regenerative therapeutic target for normal aging and in particular for a variety of neurodegenerative and neuropsychiatric diseases, including schizophrenia, obsessive-compulsive personality disorder, major depression, bipolar disorders, anxiety disorders, epilepsy, retinal degeneration, traumatic brain injury, spinal cord injury, post-traumatic stress disorder, panic disorder, Parkinson's disease, dementia, Alzheimer's disease, mild cognitive impairment, chemotherapy-induced cognitive dysfunction ("chemobrain"), Down syndrome, autism spectrum disorders, hearing loss (Neuroscience, 167 (2010) 1216-1226; Nature Medicine, Vol. 11, number 3, (2005), 271-276) tinnitus, spinocerebellar ataxia, amyotrophic lateral sclerosis, multiple sclerosis, Huntington's disease, stroke, and disturbances due to radiation therapy, chronic stress, or abuse of neuro-active drugs, such as alcohol, opiates, methamphetamine, phencyclidine and cocaine (US 2012/0022096). Hence, chemical stimulation of adult neurogenesis offers new regenerative avenues and opportunities to develop novel drugs for treating neurological diseases and neuropsychiatric disorders.

Therefore, the object of the present invention was to identify compounds that modulate neurogenesis. It has been found that the compounds of formula I are active in this area and they may therefore be used for the treatment of schizophrenia, obsessive-compulsive personality disorder, major depression, bipolar disorders, anxiety disorders, normal aging, epilepsy, retinal degeneration, traumatic brain injury, spinal cord injury, post-traumatic stress disorder, panic disorder, Parkinson's disease, dementia, Alzheimer's disease, mild cognitive impairment, chemotherapy-induced cognitive dysfunction ("chemobrain"), Down syndrome, autism spectrum disorders, hearing loss, tinnitus, spinocerebellar ataxia, amyotrophic lateral sclerosis, multiple sclerosis, Huntington's disease, stroke, and disturbances due to radiation therapy, chronic stress, or abuse of neuro-active drugs, such as alcohol, opiates, methamphetamine, phencyclidine and cocaine.

The most preferred indications for compounds of formula I are Alzheimer's disease, depression, anxiety disorders and stroke.

The present invention relates to compounds of formula I and to their pharmaceutically acceptable salts, in cases where this applies to mixtures of enantiomers or diastereomers or their enantiomerically or diastereomerically pure forms, to these compounds as pharmaceutically active substances, to the processes for their production, as well as to the use in the treatment or prevention of disorders, relating to neurogenesis, schizophrenia, obsessive-compulsive personality disorder, major depression, bipolar disorders, anxiety disorders, normal aging, epilepsy, retinal degeneration, traumatic brain injury, spinal cord injury, post-traumatic stress disorder, Parkinson's disease, dementia, Alzheimer's disease, mild cognitive impairment, chemotherapy-induced cognitive dysfunction, Down syndrome, autism spectrum disorders, hearing loss, tinnitus, spinocerebellar ataxia, amyotrophic lateral sclerosis, multiple sclerosis, Huntington's disease, stroke, radiation therapy, chronic stress, abuse of neuro-active drugs, such as alcohol, opiates, methamphetamine, phencyclidine and cocaine, and to pharmaceutical compositions containing the compounds of formula I.

The following definitions of the general terms used in the present description apply irrespective of whether the terms in question appear alone or in combination.

As used herein, the term "lower alkyl" denotes a saturated, i.e. aliphatic hydrocarbon group including a straight or branched carbon chain with 1-4 carbon atoms. Examples for "alkyl" are methyl, ethyl, n-propyl, and isopropyl.

The term "lower alkoxy" denotes a group O—R' wherein R' is lower alkyl as defined above.

The term "lower alkyl substituted by halogen" denotes a lower alkyl group as defined above and wherein at least one hydrogen atom is replaced by halogen.

The term "halogen" denotes chlorine, bromine, fluorine or iodine.

The term "pharmaceutically acceptable salt" or "pharmaceutically acceptable acid addition salt" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

One embodiment of the invention are compounds of formula

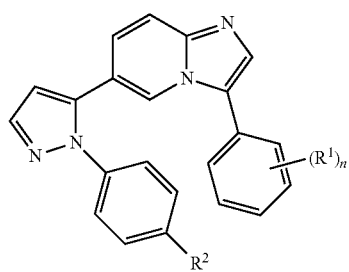

IA-1 wherein
R$^1$ is hydrogen, halogen, lower alkyl, lower alkoxy, lower alkyl substituted by halogen, cyano or S(O)$_2$-lower alkyl;
R$^2$ is hydrogen, halogen, lower alkyl, lower alkoxy, lower alkyl substituted by halogen or cyano;
n is 1 or 2;
or a pharmaceutically acceptable acid addition salt, a racemic mixture or its corresponding enantiomer and/or optical isomers thereof, for example the following compounds
3-(4-Fluoro-phenyl)-6-[2-(4-fluoro-phenyl)-2H-pyrazol-3-yl]-imidazo[1,2-a]pyridine
3-(4-Chloro-phenyl)-6-[2-(4-chloro-phenyl)-2H-pyrazol-3-yl]-imidazo[1,2-a]pyridine
6-[2-(4-Chloro-phenyl)-2H-pyrazol-3-yl]-3-(4-fluoro-phenyl)-imidazo[1,2-a]pyridine
3-(4-Chloro-phenyl)-6-[2-(4-fluoro-phenyl)-2H-pyrazol-3-yl]-imidazo[1,2-a]pyridine
3-(4-Fluoro-phenyl)-6-(2-p-tolyl-2H-pyrazol-3-yl)-imidazo[1,2-a]pyridine
3-Phenyl-6-(2-phenyl-2H-pyrazol-3-yl)-imidazo[1,2-a]pyridine
3-(4-Chloro-2-fluoro-phenyl)-6-[2-(4-fluoro-phenyl)-2H-pyrazol-3-yl]-imidazo[1,2-a]pyridine
3-Phenyl-6-(2-p-tolyl-2H-pyrazol-3-yl)-imidazo[1,2-a]pyridine
3-(4-Chloro-2-fluoro-phenyl)-6-[2-(4-chloro-phenyl)-2H-pyrazol-3-yl]-imidazo[1,2-a]pyridine
6-[2-(4-Chloro-phenyl)-2H-pyrazol-3-yl]-3-(4-methoxy-phenyl)-imidazo[1,2-a]pyridine
6-[2-(4-Fluoro-phenyl)-2H-pyrazol-3-yl]-3-(4-methoxy-phenyl)-imidazo[1,2-a]pyridine
3-(2,4-Difluoro-phenyl)-6-[2-(4-fluoro-phenyl)-2H-pyrazol-3-yl]-imidazo[1,2-a]pyridine
6-[2-(4-Chloro-phenyl)-2H-pyrazol-3-yl]-3-(2,4-difluoro-phenyl)-imidazo[1,2-a]pyridine
6-[2-(4-Chloro-phenyl)-2H-pyrazol-3-yl]-3-(4-trifluoromethyl-phenyl)-imidazo[1,2-a]pyridine
6-[2-(4-Fluoro-phenyl)-2H-pyrazol-3-yl]-3-(4-trifluoromethyl-phenyl)-imidazo[1,2-a]pyridine
4-{6-[2-(4-Fluoro-phenyl)-2H-pyrazol-3-yl]-imidazo[1,2-a]pyridin-3-yl}-benzonitrile
4-{6-[2-(4-Chloro-phenyl)-2H-pyrazol-3-yl]-imidazo[1,2-a]pyridin-3-yl}-benzonitrile
6-[2-(4-Chloro-phenyl)-2H-pyrazol-3-yl]-3-(4-methanesulfonyl-phenyl)-imidazo[1,2-a]pyridine
6-[2-(4-Fluoro-phenyl)-2H-pyrazol-3-yl]-3-(4-methanesulfonyl-phenyl)-imidazo[1,2-a]pyridine
3-(4-Fluoro-phenyl)-6-[2-(4-trifluoromethyl-phenyl)-2H-pyrazol-3-yl]-imidazo[1,2-a]pyridine or
4-{6-[2-(4-Trifluoromethyl-phenyl)-2H-pyrazol-3-yl]-imidazo[1,2-a]pyridin-3-yl}-benzonitrile.

One further embodiment of the invention are compounds of formula

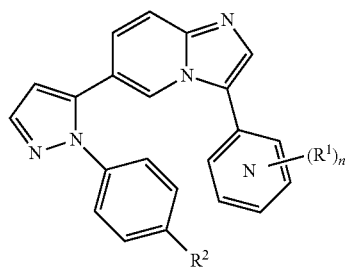

IA-2 wherein
⟨ ⟩ is a pyridine group, wherein the N-atom may be in 2, 3 or 4 position;
R$^1$ is hydrogen, halogen, lower alkyl, lower alkoxy, lower alkyl substituted by halogen, cyano or S(O)$_2$-lower alkyl;
R$^2$ is hydrogen, halogen, lower alkyl, lower alkoxy, lower alkyl substituted by halogen or cyano;
n is 1 or 2;
or a pharmaceutically acceptable acid addition salt, a racemic mixture or its corresponding enantiomer and/or optical isomers thereof, for example the compounds
6-[2-(4-Fluoro-phenyl)-2H-pyrazol-3-yl]-3-pyridin-4-yl-imidazo[1,2-a]pyridine or
6-[2-(4-Chloro-phenyl)-2H-pyrazol-3-yl]-3-pyridin-4-yl-imidazo[1,2-a]pyridine.

One further embodiment of the invention are compounds of formula

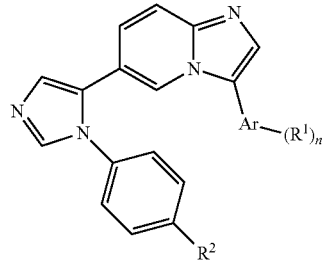

IB wherein

Ar is phenyl or pyridinyl;

R¹ is hydrogen, halogen, lower alkyl, lower alkoxy, lower alkyl substituted by halogen, cyano or S(O)₂-lower alkyl;

R² is hydrogen, halogen, lower alkyl, lower alkoxy, lower alkyl substituted by halogen or cyano;

n is 1 or 2;

or a pharmaceutically acceptable acid addition salt, a racemic mixture or its corresponding enantiomer and/or optical isomers thereof, for example the compound 3-(4-Fluoro-phenyl)-6-[3-(4-fluoro-phenyl)-3H-imidazol-4-yl]-imidazol[1,2-a]pyridine.

The present compounds of formula I and their pharmaceutically acceptable salts can be prepared by methods known in the art, for example, by processes described below, which process comprises a) reacting a compound of formula

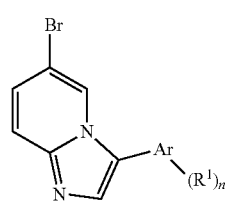

1 with a compound of formula

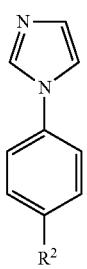

2 to a compound of formula

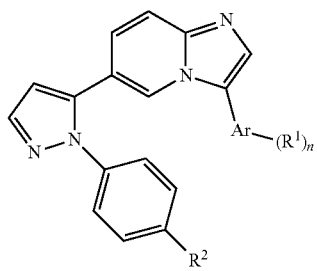

IA and, if desired, converting the compounds obtained into pharmaceutically acceptable acid addition salts.

b) reacting a compound of formula

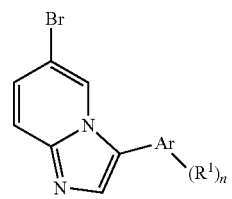

1 with a compound of formula

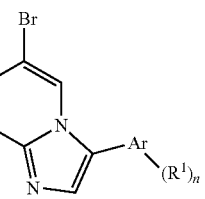

5 to a compound of formula

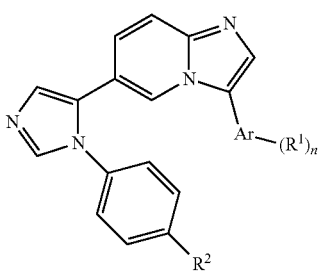

IB and, if desired, converting the compounds obtained into pharmaceutically acceptable acid addition salts.

The preparation of compounds of formula I of the present invention may be carried out in sequential or convergent synthetic routes. Syntheses of the compounds of the invention are shown in the following scheme 1. The skills required for carrying out the reaction and purification of the resulting products are known to those skilled in the art. The substituents and indices used in the following description of the processes have the significance given herein before unless indicated to the contrary.

In more detail, the compounds of formula I can be manufactured by the methods given below, by the methods given in the examples or by analogous methods. Appropriate reaction conditions for the individual reaction steps are known to a person skilled in the art. The reaction sequence is not limited to the one displayed in scheme 1, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

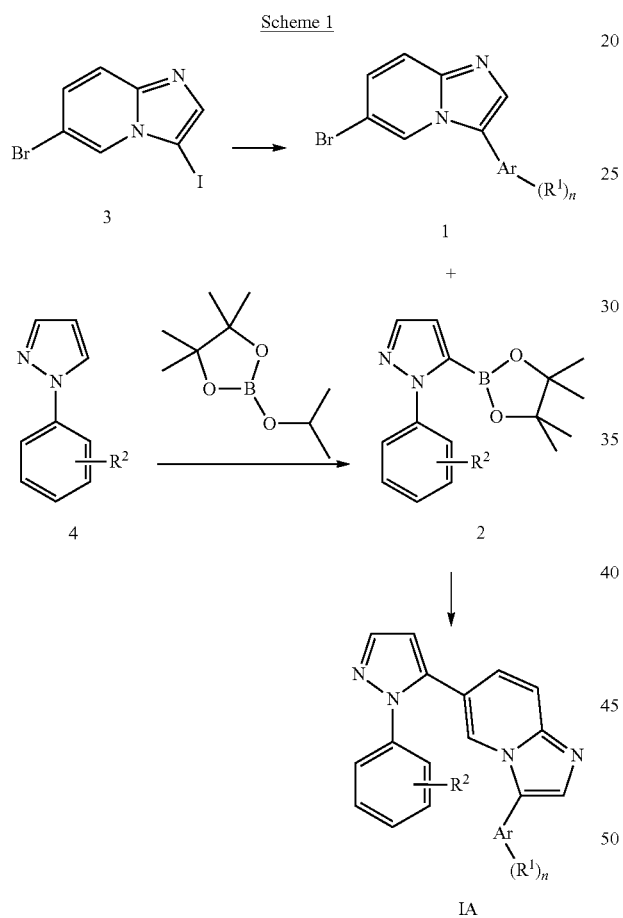

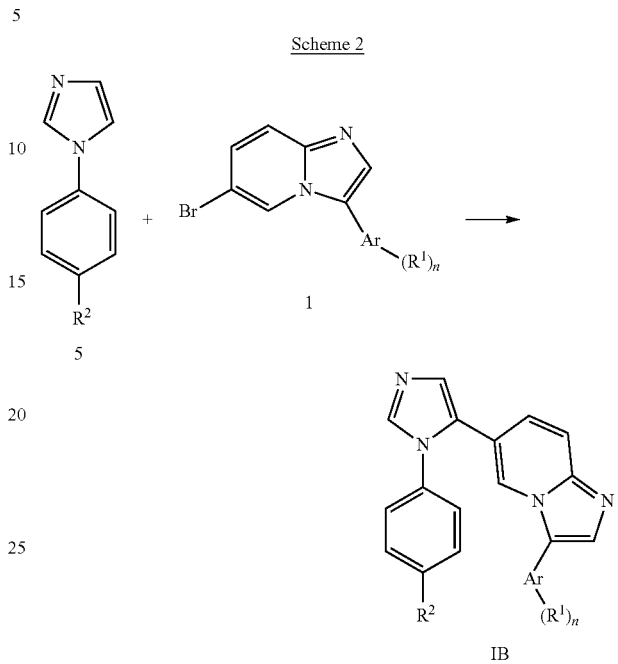

To a stirred solution of commercially available compound of formula 4 in a solvent, for example THF is added drop wise at −78° C. under argon atmosphere n-butyl lithium, for example in hexane. The reaction mixture is allowed to stir for 1 h at −78° C. Afterwards commercially available 2-isopropoxy-4,4,5,5-tetramethyl-1,3,2-dioxaborolane is added drop wise at −78° C., and the mixture is stirred for 1.5 h at −78° C. The mixture is allowed to reach room temperature within 1 h, and acetic acid is added. The mixture is purified in conventional manner to obtain a compound of formula 2.

To a mixture of compound of formula 1 and a compound of formula 2 in 1,2-dimethoxyethane is added $Na_2CO_3$ and the reaction mixture is purged with argon for 10 min in an ultrasonic bath. Afterwards tetrakis(triphenylphosphine)palladium(0) is added, and the stirred reaction mixture was heated to obtain the compound of formula IA.

To a flame-dried reaction flask are added at room temperature and under an argon atmosphere commercially available imidazole of formula 5, palladium(II)acetate, cesium fluoride, triphenylarsine and a compound of formula 1. Afterwards DMF is added successively by syringe at room temperature and under a stream of argon. The resulting mixture is allowed to stir at 140° C. under an argon atmosphere for 24 h. The reaction mixture is cooled to room temperature to obtain a compound of formula IB.

Isolation and Purification of the Compounds

Isolation and purification of the compounds and intermediates described herein can be effected, if desired, by any suitable separation or purification procedure such as, for example, filtration, extraction, crystallization, column chromatography, thin-layer chromatography, thick-layer chromatography, preparative low or high-pressure liquid chromatography or a combination of these procedures. Specific illustrations of suitable separation and isolation procedures can be had by reference to the preparations and examples herein below. However, other equivalent separation or isolation procedures could, of course, also be used. Racemic mixtures of chiral compounds of formula I can be separated using chiral HPLC.

Salts of Compounds of Formula I

The compounds of formula I are basic and may be converted to a corresponding acid addition salt. The conversion is accomplished by treatment with at least a stoichiometric amount of an appropriate acid, such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Typically, the free base is dissolved in an inert organic solvent such as diethyl ether, ethyl acetate, chloroform, ethanol or methanol and the like, and the acid added in a similar solvent. The temperature is maintained between 0° C. and 50° C. The resulting salt precipitates spontaneously or may be brought out of solution with a less polar solvent.

The acid addition salts of the basic compounds of formula I may be converted to the corresponding free bases by treatment with at least a stoichiometric equivalent of a suitable base such as sodium or potassium hydroxide, potassium carbonate, sodium bicarbonate, ammonia, and the like.

The compounds of formula I and their pharmaceutically usable addition salts possess valuable pharmacological properties. Specifically, it has been found that the compounds of the present invention have an activity as neurogenic agents.

The compounds were investigated in accordance with the test given hereinafter.

Neurogenesis Assay

Neural Stem Cell Proliferation Assay

Neurogenic properties of small molecules are determined based on the proliferation of human embryonic stem cell derived neural stem cells (NSCs) which were derived via a dual smad inhibition as previously described (Chambers, S. M., et al., *Highly efficient neural conversion of human ES and iPS cells by dual inhibition of SMAD signaling*, Nature biotechnology, 2009. 27(3): p. 275-80.)

Compounds respond is measured by the increase in cells based on ATP levels (Promega:CellTiterGlo®) after an incubation period of 4 days.

NSCs are thawed and expanded over 3 passages. On the 14$^{th}$ day, NSCs are seeded in Polyornithin/Laminin coated 384 well plates at a cell density of 21'000 cells/cm$^2$ in a media volume of 38 µl.

4 hours after cell seeding, compound solutions are added at a volume of 2 µl. Stock solutions of the compounds (water, 5% DMSO) are diluted to obtain a dose response (11 points, dilution factor is 2), ranging from 8 µM to 8 nM. Controls are run to consistently determine the neurogenic properties of the cells:

Negative (neutral) control is cell culture Media (final DMSO concentration: 0.25%). Positive controls are:
1. cell culture Media+100 ng/ml FGF2 (final DMSO concentration: 0.1%)
2. cell culture Media+20 ng/ml EGF (final DMSO concentration: 0.1%)
3. cell culture Media+100 ng/ml Wnt3a (final DMSO concentration: 0.1%)

After 4 days incubation at 37° C., 5% $CO_2$, the amount of ATP per well is quantified. The ATP concentration is proportional to the cell number. ATP is quantified by using the Promega CellTiterGlo® kit. The CellTiterGlo® reagents contain a cell lysis buffer, a thermo stable luciferase (Ultra-Glo™ recombinant luciferase), magnesium and luciferin. Luciferin reacts with ATP producing oxyluciferin, AMP and light. The luminescence signal is proportional to the ATP content.

The value of negative (neutral) control is determined for each assay plate by taking the average of 16 negative control wells. The neurogenic compound response is calculated for each compound as (compound/Negative Control)* 100.

The values of $EC_{150}$ from the dose response curve are determined for each test compound. The $EC_{150}$ is the compound concentration at which 150% activity of control (100%) is reached. The preferred compounds show a $EC_{150}$ (µM) in the range of <2.8 µM as shown in the table below.

List of Examples and $EC_{150}$ Data

| Ex. | Structure | Name | $EC_{150}$ (uM) |
|---|---|---|---|
| 1 | 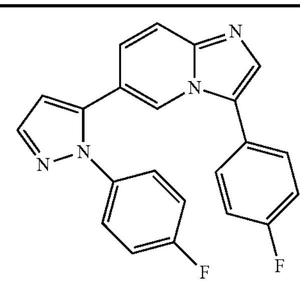 | 3-(4-Fluoro-phenyl)-6-[2-(4-fluoro-phenyl)-2H-pyrazol-3-yl]-imidazo[1,2-a]pyridine | 0.019 |
| 2 | 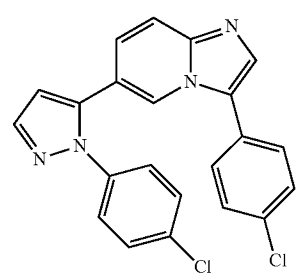 [SMILES: Clc1ccc(-c2cnc3ccc(-c4ccnn4-c4ccc(Cl)cc4)cn23)cc1] | 3-(4-Chloro-phenyl)-6-[2-(4-chloro-phenyl)-2H-pyrazol-3-yl]-imidazo[1,2-a]pyridine | 0.1 |

-continued

| Ex. | Structure | Name | EC$_{150}$ (uM) |
|---|---|---|---|
| 3 | 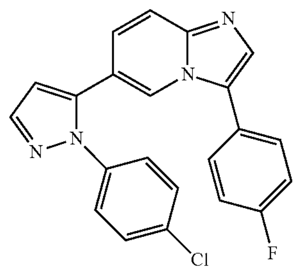 [SMILES: Fc1ccc(-c2cnc3ccc(-c4ccnn4-c4ccc(Cl)cc4)cn23)cc1] | 6-[2-(4-Chloro-phenyl)-2H-pyrazol-3-yl]-3-(4-fluoro-phenyl)-imidazo[1,2-a]pyridine | 0.096 |
| 4 | 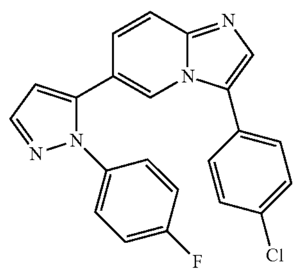 [SMILES: Fc1ccc(-n2nccc2-c2ccc3ncc(-c4ccc(Cl)cc4)n3c2)cc1] | 3-(4-Chloro-phenyl)-6-[2-(4-fluoro-phenyl)-2H-pyrazol-3-yl]-imidazo[1,2-a]pyridine | 0.092 |
| 5 | 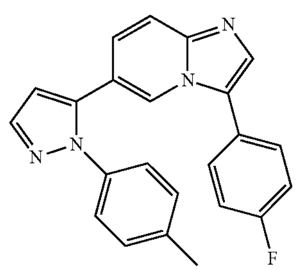 [SMILES: Cc1ccc(-n2nccc2-c2ccc3ncc(-c4ccc(F)cc4)n3c2)cc1] | 3-(4-Fluoro-phenyl)-6-(2-p-tolyl-2H-pyrazol-3-yl)-imidazo[1,2-a]pyridine | 0.008 |
| 6 | 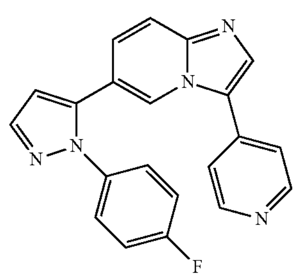 [SMILES: Fc1ccc(-n2nccc2-c2ccc3ncc(-c4ccncc4)n3c2)cc1] | 6-[2-(4-Fluoro-phenyl)-2H-pyrazol-3-yl]-3-pyridin-4-yl-imidazo[1,2-a]pyridine | 0.026 |
| 7 | 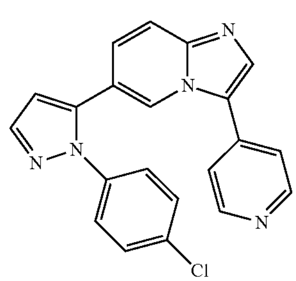 [SMILES: Clc1ccc(-n2nccc2-c2ccc3ncc(-c4ccncc4)n3c2)cc1] | 6-[2-(4-Chloro-phenyl)-2H-pyrazol-3-yl]-3-pyridin-4-yl-imidazo[1,2-a]pyridine | 0.022 |

-continued

| Ex. | Structure | Name | EC$_{150}$ (uM) |
|---|---|---|---|
| 8 | 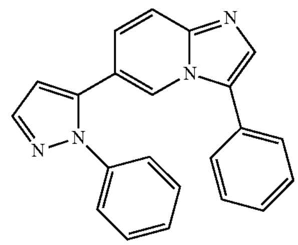 [SMILES: c1ccc(-c2cnc3ccc(-c4ccnn4-c4ccccc4)cn23)cc1] | 3-Phenyl-6-(2-phenyl-2H-pyrazol-3-yl)-imidazo[1,2-a]pyridine | 0.019 |
| 9 | 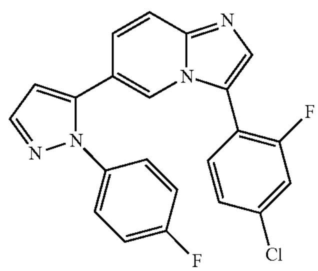 [SMILES: Fc1ccc(-n2nccc2-c2ccc3ncc(-c4ccc(Cl)cc4F)n3c2)cc1] | 3-(4-Chloro-2-fluoro-phenyl)-6-[2-(4-fluoro-phenyl)-2H-pyrazol-3-yl]-imidazo[1,2-a]pyridine | 0.055 |
| 10 | 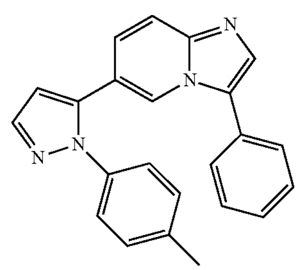 [SMILES: Cc1ccc(-n2nccc2-c2ccc3ncc(-c4ccccc4)n3c2)cc1] | 3-Phenyl-6-(2-p-tolyl-2H-pyrazol-3-yl)-imidazo[1,2-a]pyridine | 0.009 |
| 11 | 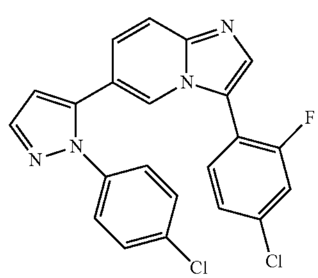 [SMILES: Fc1cc(Cl)ccc1-c1cnc2ccc(-c3ccnn3-c3ccc(Cl)cc3)cn12] | 3-(4-Chloro-2-fluoro-phenyl)-6-[2-(4-chloro-phenyl)-2H-pyrazol-3-yl]-imidazo[1,2-a]pyridine | 0.089 |
| 12 | 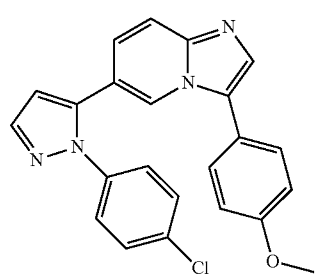 [SMILES: COc1ccc(-c2cnc3ccc(-c4ccnn4-c4ccc(Cl)cc4)cn23)cc1] | 6-[2-(4-Chloro-phenyl)-2H-pyrazol-3-yl]-3-(4-methoxy-phenyl)-imidazo[1,2-a]pyridine | 0.045 |

-continued

| Ex. | Structure | Name | EC$_{150}$ (uM) |
|---|---|---|---|
| 13 | 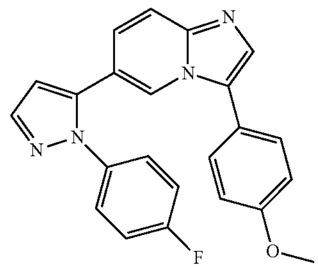 [SMILES: COc1ccc(-c2cnc3ccc(-c4ccnn4-c4ccc(F)cc4)cn23)cc1] | 6-[2-(4-Fluoro-phenyl)-2H-pyrazol-3-yl]-3-(4-methoxy-phenyl)-imidazo[1,2-a]pyridine | 0.024 |
| 14 | 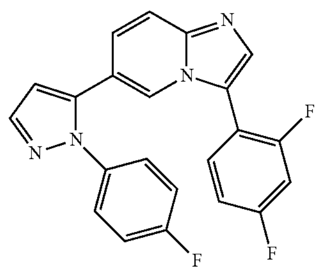 [SMILES: Fc1ccc(-n2nccc2-c2ccc3ncc(-c4ccc(F)cc4F)n3c2)cc1] | 3-(2,4-Difluoro-phenyl)-6-[2-(4-fluoro-phenyl)-2H-pyrazol-3-yl]-imidazo[1,2-a]pyridine | 0.053 |
| 15 | 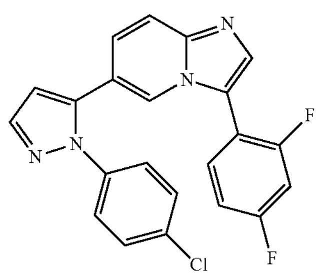 | 6-[2-(4-Chloro-phenyl)-2H-pyrazol-3-yl]-3-(2,4-difluoro-phenyl)-imidazo[1,2-a]pyridine | 0.029 |
| 16 | 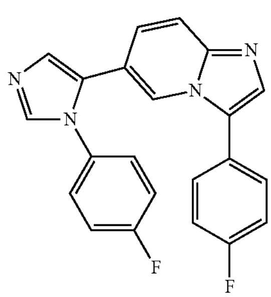 [SMILES: Fc1ccc(-c2cnc3ccc(-c4cncn4-c4ccc(F)cc4)cn23)cc1] | 3-(4-Fluoro-phenyl)-6-[3-(4-fluoro-phenyl)-3H-imidazol-4-yl]-imidazo[1,2-a]pyridine | 0.053 |
| 17 | 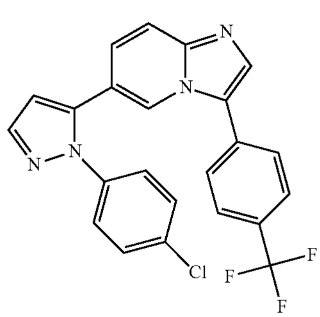 | 6-[2-(4-Chloro-phenyl)-2H-pyrazol-3-yl]-3-(4-trifluoromethyl-phenyl)-imidazo[1,2-a]pyridine | 0.38 |

-continued

| Ex. | Structure | Name | EC$_{150}$ (uM) |
|---|---|---|---|
| 18 | 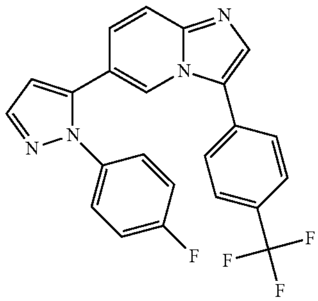 [SMILES: Fc1ccc(-n2nccc2-c2ccc3ncc(-c4ccc(C(F)(F)F)cc4)n3c2)cc1] | 6-[2-(4-Fluoro-phenyl)-2H-pyrazol-3-yl]-3-(4-trifluoromethyl-phenyl)-imidazo[1,2-a]pyridine | 0.18 |
| 19 | 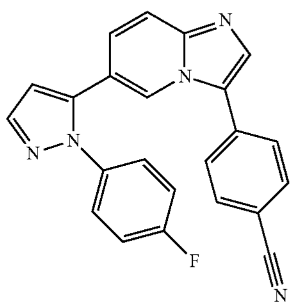 | 4-{6-[2-(4-Fluoro-phenyl)-2H-pyrazol-3-yl]-imidazo[1,2-a]pyridin-3-yl}-benzonitrile | 0.03 |
| 20 | 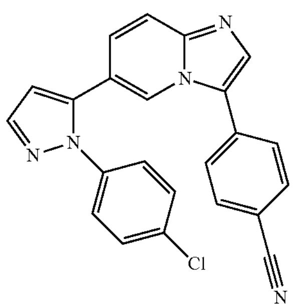 [SMILES: N#Cc1ccc(-c2cnc3ccc(-c4ccnn4-c4ccc(Cl)cc4)cn23)cc1] | 4-{6-[2-(4-Chloro-phenyl)-2H-pyrazol-3-yl]-imidazo[1,2-a]pyridin-3-yl}-benzonitrile | 0.04 |
| 21 | 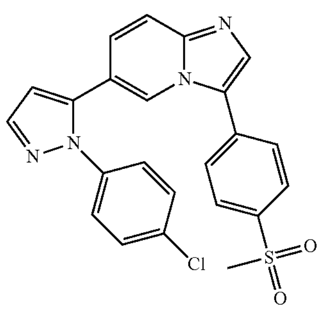 [SMILES: CS(=O)(=O)c1ccc(-c2cnc3ccc(-c4ccnn4-c4ccc(Cl)cc4)cn23)cc1] | 6-[2-(4-Chloro-phenyl)-2H-pyrazol-3-yl]-3-(4-methanesulfonyl-phenyl)-imidazo[1,2-a]pyridine | 0.25 |
| 22 | 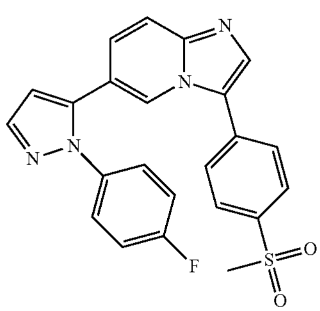 [SMILES: CS(=O)(=O)c1ccc(-c2cnc3ccc(-c4ccnn4-c4ccc(F)cc4)cn23)cc1] | 6-[2-(4-Fluoro-phenyl)-2H-pyrazol-3-yl]-3-(4-methanesulfonyl-phenyl)-imidazo[1,2-a]pyridine | 0.24 |

| Ex. | Structure | Name | EC$_{150}$ (uM) |
|---|---|---|---|
| 23 | 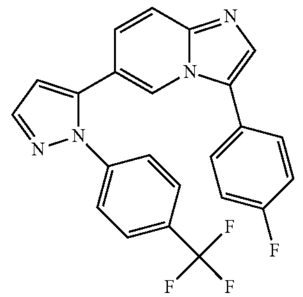 [SMILES: Fc1ccc(-c2cnc3ccc(-c4ccnn4-c4ccc(C(F)(F)F)cc4)cn23)cc1] | 3-(4-Fluoro-phenyl)-6-[2-(4-trifluoromethyl-phenyl)-2H-pyrazol-3-yl]-imidazo[1,2-a]pyridine | 0.79 |
| 24 | 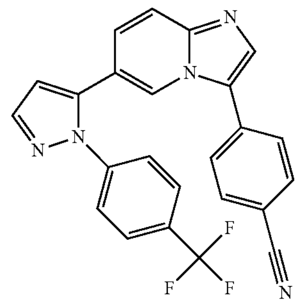 [SMILES: N#Cc1ccc(-c2cnc3ccc(-c4ccnn4-c4ccc(C(F)(F)F)cc4)cn23)cc1] | 4-{6-[2-(4-Trifluoromethyl-phenyl)-2H-pyrazol-3-yl]-imidazo[1,2-a]pyridin-3-yl}-benzonitrile | 2.6 |

Intermediates

Intermediate A: 1-(4-Fluoro-phenyl)-5-(4,4,5,5-tetramethyl-[1,3,2]dioxaborolan-2-yl)-1H-pyrazole

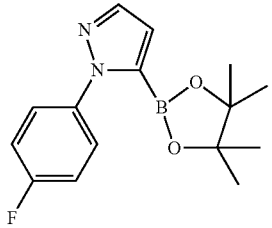 [SMILES: CC1(C)OB(c2ccnn2-c2ccc(F)cc2)OC1(C)C]

To a stirred solution of commercially available 1-(4-fluorophenyl)-1H-pyrazole [CAS No 81329-32-0] (2.27 g, 14.0 mmol) in THF (100 ml) was added drop wise at −78° C. under argon atmosphere n-butyl lithium (1.6N in hexane, 10.5 ml, 16.8 mmol. The reaction mixture was allowed to stir for 1 h at −78° C. Afterwards commercially available 2-isopropoxy-4,4,5,5-tetramethyl-1,3,2-dioxaborolane (2.84 g, 3.12 ml, 15.0 mmol) was added drop wise at −78° C., and the mixture was stirred for 1.5 h at −78° C. The mixture was allowed to reach room temperature within 1 h, and acetic acid (0.925 g, 881 µl, 15.4 mmol) was added. The mixture was filtered using a Celite pad, which was washed with ethyl acetate, and the filtrate was evaporated to dryness. The crude product (4.36 g, light brown solid) was purified by flash chromatography on silica gel (heptane/ethyl acetate, 10-50%) to yield the title compound as an off-white solid (2.04 g, 51%), MS (ISP) m/z=289.5 [(M+H)$^+$], mp 133° C.

Intermediate B: 1-(4-Chloro-phenyl)-5-(4,4,5,5-tetramethyl-[1,3,2]dioxaborolan-2-yl)-1H-pyrazole

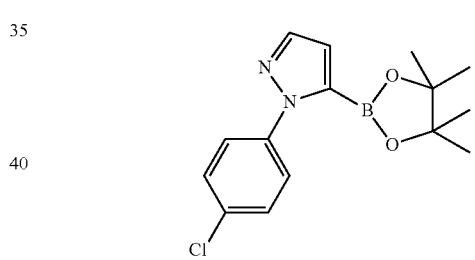

The title compound, light brown solid (1.27 g, 45%), MS (ISP) m/z=305.4 [(M+H)$^+$], mp 170° C., was prepared in accordance with the general method of intermediate A from commercially available 1-(4-chlorophenyl)-1H-pyrazol [CAS No. 25419-86-7] (1.66 g, 9.29 mmol) and commercially available 2-isopropoxy-4,4,5,5-tetramethyl-1,3,2-dioxaborolane.

Intermediate C: 5-(4,4,5,5-Tetramethyl-[1,3,2]dioxaborolan-2-yl)-1-p-tolyl-1H-pyrazole

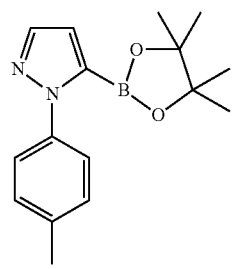 [SMILES: Cc1ccc(-n2nccc2B2OC(C)(C)C(C)(C)O2)cc1]

The title compound, light brown solid (2.31 g, 85%), MS (ISP) m/z=285.6 [(M+H)⁺], mp 127° C., was prepared in accordance with the general method of intermediate A from commercially available 1-(p-tolyl)-1H-pyrazole [CAS No. 20518-17-6] (1.51 g, 9.54 mmol) and commercially available 2-isopropoxy-4,4,5,5-tetramethyl-1,3,2-dioxaborolane.

Intermediate D: 1-Phenyl-5-(4,4,5,5-tetramethyl-[1,3,2]dioxaborolan-2-yl)-1H-pyrazole

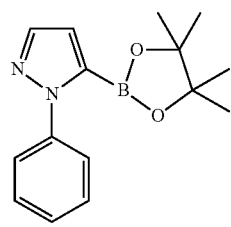 [SMILES: CC1(C)OB(c2ccnn2-c2ccccc2)OC1(C)C]

The title compound, brown solid (2.0 g, 76%), MS (ISP) m/z=271.6 [(M+H)⁺], mp 132° C., was prepared in accordance with the general method of intermediate A from commercially available 1-phenyl-1H-pyrazol (1.40 g, 9.71 mmol) and commercially available 2-isopropoxy-4,4,5,5-tetramethyl-1,3,2-dioxaborolane.

Intermediate E: 6-Bromo-3-(4-fluoro-phenyl)-imidazo[1,2-a]pyridine

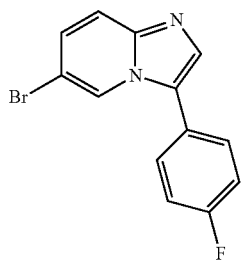 [SMILES: Fc1ccc(-c2cnc3ccc(Br)cn23)cc1]

To a mixture of commercially available 6-bromo-3-iodoimidazo[1,2-a]pyridine (0.7 g, 2.17 mmol) and commercially available 4-fluoro-phenylboronic acid (0.3 g, 2.17 mmol) in 1,2-dimethoxyethane (14 ml), 2M sodium carbonate solution (2.71 ml, 5.42 mmol) was added, and the reaction mixture was purged with argon for 5 min in an ultrasonic bath. Afterwards tetrakis(triphenylphosphine)palladium(0) (125 mg, 108 µmol) was added, and the stirred reaction mixture was heated under reflux conditions for 17 h. The reaction mixture was cooled to room temperature, poured into water (30 ml) and extracted with ethyl acetate (2×40 ml). The combined organic layers were washed with brine (30 ml), dried (MgSO₄) and evaporated. The crude material (0.74 g) was further purified by flash chromatography on silica gel (dichloromethane/MeOH 98:2) and trituration (diethyl ether) to yield the title compound as a light yellow solid (0.3 g, 48%), MS (ISP) m/z=291.3 [(M+H)⁺], mp 102° C.

Intermediate F: 6-Bromo-3-(4-chloro-phenyl)-imidazo[1,2-a]pyridine

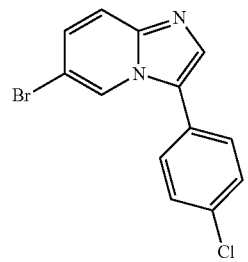 [SMILES: Clc1ccc(-c2cnc3ccc(Br)cn23)cc1]

The title compound, light yellow solid (0.28 g, 42%), MS (ISP) m/z=307.3 [(M+H)⁺], mp 157° C., was prepared in accordance with the general method of intermediate E from commercially available 6-bromo-3-iodoimidazo[1,2-a]pyridine (0.7 g, 2.17 mmol) and commercially available 4-chlorophenylboronic acid (0.34 g, 2.17 mmol).

Intermediate G: 6-Bromo-3-phenyl-imidazo[1,2-a]pyridine

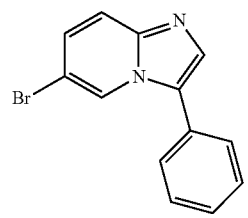 [SMILES: Brc1ccc2ncc(-c3ccccc3)n2c1]

The title compound, off-white solid (0.4 g, 68%), MS (ISP) m/z=273.4 [(M+H)⁺], mp 77° C., was prepared in accordance with the general method of intermediate E from commercially available 6-bromo-3-iodoimidazo[1,2-a]pyridine (0.7 g, 2.17 mmol) and commercially available phenylboronic acid (0.29 g, 2.38 mmol).

Intermediate H: 6-Bromo-3-pyridin-4-yl-imidazo[1,2-a]pyridine

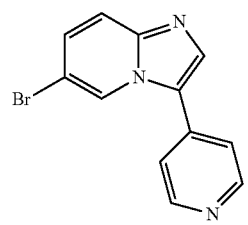 [SMILES: Brc1ccc2ncc(-c3ccncc3)n2c1]

The title compound, off-white solid (0.27 g, 45%), MS (ISP) m/z=274.4 [(M+H)⁺], mp 134° C., was prepared in accordance with the general method of intermediate E from commercially available 6-bromo-3-iodoimidazo[1,2-a]pyridine (0.7 g, 2.17 mmol) and commercially available pyridine-4-ylboronic acid (0.27 g, 2.17 mmol).

Intermediate I: 6-Bromo-3-(4-chloro-2-fluoro-phenyl)-imidazo[1,2-a]pyridine

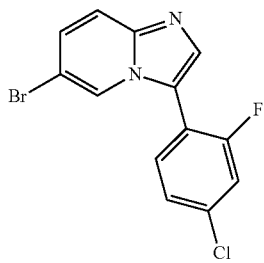 [SMILES: Fc1cc(Cl)ccc1-c1cnc2ccc(Br)cn12]

The title compound, light brown solid (0.54 g, 76%), MS (ISP) m/z=327.3 [(M+H)+], mp 159° C., was prepared in accordance with the general method of intermediate E from commercially available 6-bromo-3-iodoimidazo[1,2-a]pyridine (0.7 g, 2.17 mmol) and commercially available 4-chloro-2-fluoro-phenylboronic acid (0.42 g, 2.38 mmol).

Intermediate K: 6-Bromo-3-(2,4-difluoro-phenyl)-imidazo[1,2-a]pyridine

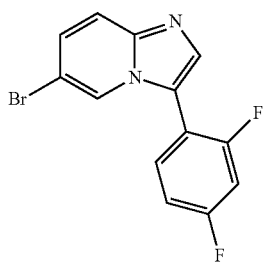 [SMILES: Fc1ccc(-c2cnc3ccc(Br)cn23)c(F)c1]

The title compound, off-white solid (0.33 g, 49%), MS (ISP) m/z=309.4 [(M+H)+], mp 137.5° C., was prepared in accordance with the general method of intermediate E from commercially available 6-bromo-3-iodoimidazo[1,2-a]pyridine (0.7 g, 2.17 mmol) and commercially available 2,4-difluoro-phenylboronic acid (0.38 g, 2.38 mmol).

Intermediate L: 6-Bromo-3-(4-methoxy-phenyl)-imidazo[1,2-a]pyridine

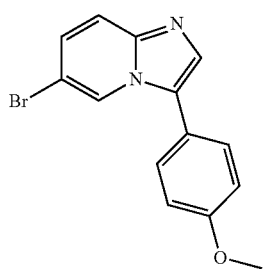 [SMILES: COc1ccc(-c2cnc3ccc(Br)cn23)cc1]

The title compound, brown oil (0.47 g, 72%), MS (ISP) m/z=303.4 [(M+H)+], was prepared in accordance with the general method of intermediate E from commercially available 6-bromo-3-iodoimidazo[1,2-a]pyridine (0.7 g, 2.17 mmol) and commercially available 4-methoxy-phenylboronic acid (0.36 g, 2.38 mmol).

Intermediate M: 6-Bromo-3-(4-trifluoromethyl-phenyl)-imidazo[1,2-a]pyridine

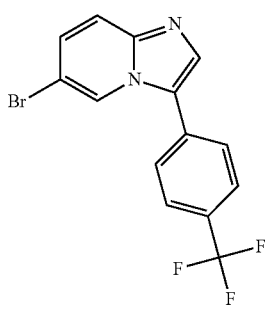 [SMILES: FC(F)(F)c1ccc(-c2cnc3ccc(Br)cn23)cc1]

The title compound, light brown solid (0.3 g, 40%), MS (ISP) m/z=341.4 [(M+H)+], mp 151° C., was prepared in accordance with the general method of intermediate E from commercially available 6-bromo-3-iodoimidazo[1,2-a]pyridine (0.7 g, 2.17 mmol) and commercially available 4-trifluoromethyl-phenylboronic acid (0.45 g, 2.38 mmol).

Intermediate N: 4-(6-Bromo-imidazo[1,2-a]pyridin-3-yl)-benzonitrile

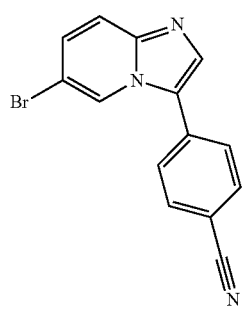 [SMILES: N#Cc1ccc(-c2cnc3ccc(Br)cn23)cc1]

The title compound, light brown solid (0.47 g, 73%), MS (ISP) m/z=298.4 [(M+H)+], mp 176° C., was prepared in accordance with the general method of intermediate E from commercially available 6-bromo-3-iodoimidazo[1,2-a]pyridine (0.7 g, 2.17 mmol) and commercially available 4-cyano-phenylboronic acid (0.36 g, 2.38 mmol).

Intermediate O: 6-Bromo-3-(4-methanesulfonyl-phenyl)-imidazo[1,2-a]pyridine

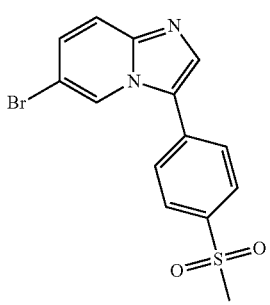 [SMILES: CS(=O)(=O)c1ccc(-c2cnc3ccc(Br)cn23)cc1]

The title compound, brown solid (0.53 g, 69%), MS (ISP) m/z=353.4 [(M+H)⁺], mp 194° C., was prepared in accordance with the general method of intermediate E from commercially available 6-bromo-3-iodoimidazo[1,2-a]pyridine (0.7 g, 2.17 mmol) and commercially available 4-methanesulfonyl-phenylboronic acid (0.48 g, 2.38 mmol).

Intermediate P: 5-(4,4,5,5-Tetramethyl-[1,3,2]dioxaborolan-2-yl)-1-(4-trifluoromethyl-phenyl)-1H-pyrazole

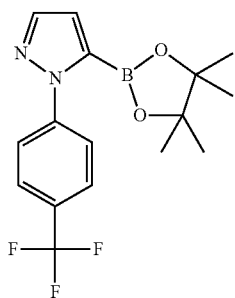 [SMILES: CC1(C)OB(c2ccnn2-c2ccc(C(F)(F)F)cc2)OC1(C)C]

The title compound, light yellow solid (2.21 g, 69%), MS (ISN) m/z=338.6 [(M-H)⁺], mp 153° C., was prepared in accordance with the general method of intermediate A from commercially available 1-(4-(trifluoromethyl)-phenyl)-1H-pyrazol [CAS No. 207797-05-5] (2 g, 9.43 mmol) and commercially available 2-isopropoxy-4,4,5,5-tetramethyl-1,3,2-dioxaborolane.

EXAMPLE 1

3-(4-Fluoro-phenyl)-6-[2-(4-fluoro-phenyl)-2H-pyrazol-3-yl]-imidazo[1,2-a]pyridine

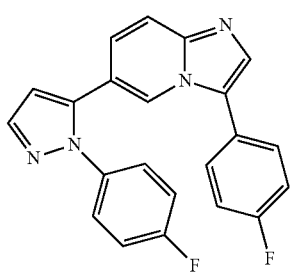 [SMILES: Fc1ccc(-c2cnc3ccc(-c4ccnn4-c4ccc(F)cc4)cn23)cc1]

To a mixture of 6-bromo-3-(4-fluorophenyl)-imidazo[1,2-a]pyridine (intermediate E) (100 mg, 344 μmol) and 1-(4-fluoro-phenyl)-5-(4,4,5,5-tetramethyl-1,3,2-dioxaborolan-2-yl)-1H-pyrazole (intermediate A) (119 mg, 412 μl) in 1,2-dimethoxyethane (2 ml), was added 1M Na₂CO₃ (859 μl, 859 μmol), and the reaction mixture was purged with argon for 10 min in an ultrasonic bath. Afterwards tetrakis(triphenylphosphine)palladium(0) (39.7 mg, 34.4 μmol) was added, and the stirred reaction mixture was heated under reflux conditions for 17 h. The reaction mixture was cooled to room temperature, poured into water (20 ml) and extracted with ethyl acetate (2×20 ml). The combined organic layers were washed with brine (20 ml), dried (MgSO₄) and evaporated. The crude material (190 mg) was further purified by flash chromatography on silica gel (dichloromethane/MeOH, 0-20%) and trituration (diethyl ether) to yield the title compound as an off-white solid (40 mg, 31%), MS (ISP) m/z=373.4 [(M+H)⁺], mp 172° C.

EXAMPLE 2

3-(4-Chloro-phenyl)-6-[2-(4-chloro-phenyl)-2H-pyrazol-3-yl]-imidazo[1,2-a]pyridine

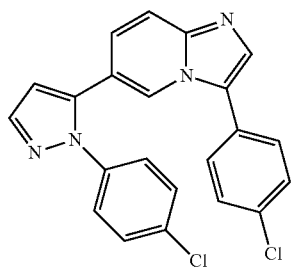 [SMILES: Clc1ccc(-c2cnc3ccc(-c4ccnn4-c4ccc(Cl)cc4)cn23)cc1]

The title compound, off-white solid (41 mg, 31%), MS (ISP) m/z=405.3 [(M+H)⁺], mp 172.5° C., was prepared in accordance with the general method of example 1 from 6-bromo-3-(4-chloro-phenyl)-imidazo[1,2-a]pyridine (intermediate F) (0.1 g, 0.325 mmol) and 1-(4-chloro-phenyl)-5-(4,4,5,5-tetramethyl-[1,3,2]dioxaborolan-2-yl)-1H-pyrazole (intermediate B) (0.12 g, 0.39 mmol).

EXAMPLE 3

6-[2-(4-Chloro-phenyl)-2H-pyrazol-3-yl]-3-(4-fluoro-phenyl)-imidazo[1,2-a]pyridine

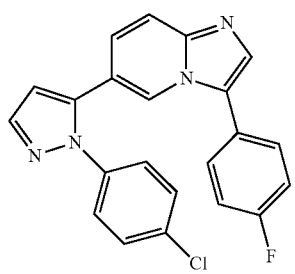 [SMILES: Fc1ccc(-c2cnc3ccc(-c4ccnn4-c4ccc(Cl)cc4)cn23)cc1]

The title compound, white solid (27 mg, 20%), MS (ISP) m/z=389.4 [(M+H)⁺], mp 147° C., was prepared in accordance with the general method of example 1 from 6-bromo-3-(4-fluoro-phenyl)-imidazo[1,2-a]pyridine (intermediate E) (0.1 mg, 0.34 mmol) and 1-(4-chloro-phenyl)-5-(4,4,5,5-tetramethyl-[1,3,2]dioxaborolan-2-yl)-1H-pyrazole (intermediate B) (0.13 g, 0.41 mmol).

EXAMPLE 4

3-(4-Chloro-phenyl)-6-[2-(4-fluoro-phenyl)-2H-pyrazol-3-yl]-imidazo [1,2-a]pyridine

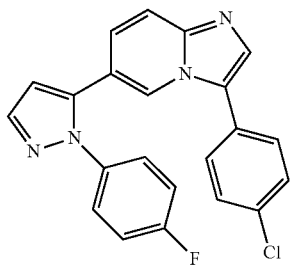 [SMILES: Fc1ccc(-n2nccc2-c2ccc3ncc(-c4ccc(Cl)cc4)n3c2)cc1]

The title compound, off-white solid (43 mg, 34%), MS (ISP) m/z=389.4 [(M+H)⁺], mp 171° C., was prepared in accordance with the general method of example 1 from 6-bromo-3-(4-chloro-phenyl)-imidazo[1,2-a]pyridine (intermediate F) (0.1 g, 0.325 mmol) and 1-(4-fluorophenyl)-5-(4,4,5,5-tetramethyl-1,3,2-dioxaborolan-2-yl)-1H-pyrazole (intermediate A) (0.11 mg, 0.38 mmol).

EXAMPLE 5

3-(4-Fluoro-phenyl)-6-(2-p-tolyl-2H-pyrazol-3-yl)-imidazo[1,2-a]pyridine

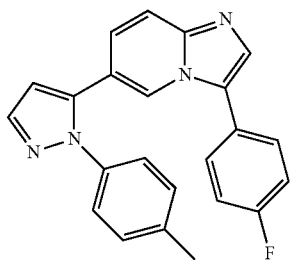 [SMILES: Cc1ccc(-n2nccc2-c2ccc3ncc(-c4ccc(F)cc4)n3c2)cc1]

The title compound, white solid (14 mg, 11%), MS (ISP) m/z=369.5 [(M+H)⁺], mp 141° C., was prepared in accordance with the general method of example 1 from 6-bromo-3-(4-fluoro-phenyl)-imidazo[1,2-a]pyridine (intermediate E) (0.1 mg, 0.34 mmol) and 5-(4,4,5,5-tetramethyl-[1,3,2]dioxaborolan-2-yl)-1-p-tolyl-1H-pyrazole (intermediate C) (0.083 g, 0.41 mmol).

EXAMPLE 6

6-[2-(4-Fluoro-phenyl)-2H-pyrazol-3-yl]-3-pyridin-4-yl-imidazo [1,2-a]pyridine

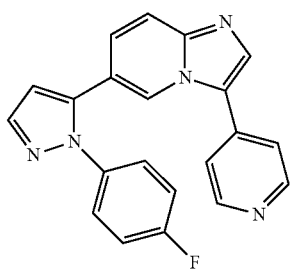 [SMILES: Fc1ccc(-n2nccc2-c2ccc3ncc(-c4ccncc4)n3c2)cc1]

The title compound, off-white solid (49 mg, 38%), MS (ISP) m/z=356.6 [(M+H)⁺], mp 201° C., was prepared in accordance with the general method of example 1 from 6-bromo-3-pyridin-4-yl-imidazo[1,2-a]pyridine (intermediate F) (0.1 g, 0.365 mmol) and 1-(4-fluoro-phenyl)-5-(4,4,5,5-tetramethyl-1,3,2-dioxaborolan-2-yl)-1H-pyrazole (intermediate A) (0.13 mg, 0.44 mmol).

EXAMPLE 7

6-[2-(4-Chloro-phenyl)-2H-pyrazol-3-yl]-3-pyridin-4-yl-imidazo[1,2-a]pyridine

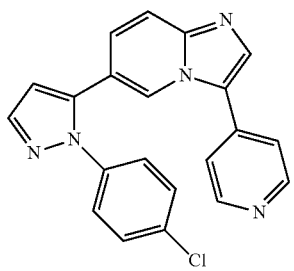

The title compound, off-white solid (37 mg, 27%), MS (ISP) m/z=372.5 [(M+H)⁺], mp 186° C., was prepared in accordance with the general method of example 1 6-bromo-3-pyridin-4-yl-imidazo[1,2-a]pyridine (intermediate F) (0.1 g, 0.365 mmol) and 1-(4-chloro-phenyl)-5-(4,4,5,5-tetramethyl-[1,3,2]dioxaborolan-2-yl)-1H-pyrazole (intermediate B) (0.13 g, 0.44 mmol).

EXAMPLE 8

3-Phenyl-6-(2-phenyl-2H-pyrazol-3-yl)-imidazo[1,2-a]pyridine

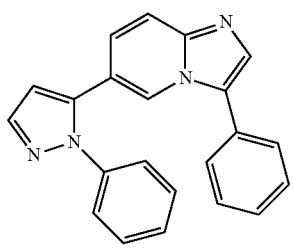 [SMILES: c1ccc(-c2cnc3ccc(-c4ccnn4-c4ccccc4)cn23)cc1]

The title compound, off-white solid (48 mg, 39%), MS (ISP) m/z=337.5 [(M+H)⁺], mp 139° C., was prepared in accordance with the general method of example 1 from 6-bromo-3-phenyl-imidazo[1,2-a]pyridine (intermediate G) (0.1 g, 0.366 mmol) and 1-phenyl-5-(4,4,5,5-tetramethyl-[1,3,2]dioxaborolan-2-yl)-1H-pyrazole (intermediate D) (0.12 g, 0.44 mmol).

EXAMPLE 9

3-(4-Chloro-2-fluoro-phenyl)-6-[2-(4-fluoro-phenyl)-2H-pyrazol-3-yl]-imidazo[1,2-a]pyridine

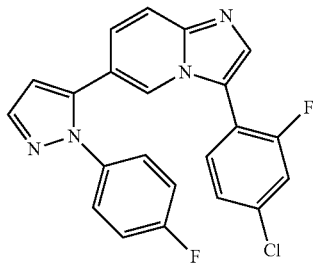 [SMILES: Fc1ccc(-n2nccc2-c2ccc3ncc(-c4ccc(Cl)cc4F)n3c2)cc1]

The title compound, white solid (53 mg, 42%), MS (ISP) m/z=407.5 [(M+H)$^+$], mp 187° C., was prepared in accordance with the general method of example 1 from 6-bromo-3-(4-chloro-2-fluoro-phenyl)-imidazo[1,2-c]pyridine (intermediate I) (0.1 g, 0.31 mmol) and 1-(4-fluoro-phenyl)-5-(4,4,5,5-tetramethyl-1,3,2-dioxaborolan-2-yl)-1H-pyrazole (intermediate A) (0.12 mg, 0.39 mmol).

EXAMPLE 10

3-Phenyl-6-(2-p-tolyl-2H-pyrazol-3-yl)-imidazo[1,2-a]pyridine

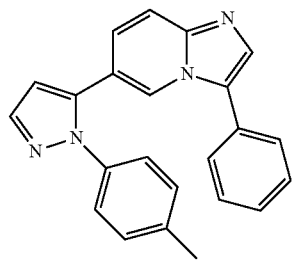 [SMILES: Cc1ccc(-n2nccc2-c2ccc3ncc(-c4ccccc4)n3c2)cc1]

The title compound, off-white solid (53 mg, 41%), MS (ISP) m/z=351.5 [(M+H)$^+$], mp 107° C., was prepared in accordance with the general method of example 1 from 6-bromo-3-phenyl-imidazo[1,2-a]pyridine (intermediate G) (0.1 g, 0.366 mmol) and 5-(4,4,5,5-tetramethyl-[1,3,2]dioxaborolan-2-yl)-1-p-tolyl-1H-pyrazole (intermediate C) (0.125 g, 0.44 mmol).

EXAMPLE 11

3-(4-Chloro-2-fluoro-phenyl)-6-[2-(4-chloro-phenyl)-2H-pyrazol-3-yl]-imidazo[1,2-a]pyridine

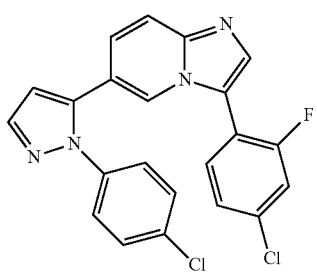

The title compound, white solid (46 mg, 46%), MS (ISP) m/z=423.5 [(M+H)$^+$], mp 148° C., was prepared in accordance with the general method of example 1 from 6-bromo-3-(4-chloro-2-fluoro-phenyl)-imidazo[1,2-a]pyridine (intermediate I) (0.1 g, 0.31 mmol) and 1-(4-chloro-phenyl)-5-(4,4,5,5-tetramethyl-[1,3,2]dioxaborolan-2-yl)-1H-pyrazole (intermediate B) (0.11 g, 0.37 mmol).

EXAMPLE 12

6-[2-(4-Chloro-phenyl)-2H-pyrazol-3-yl]-3-(4-methoxy-phenyl)-imidazo[1,2-a]pyridine

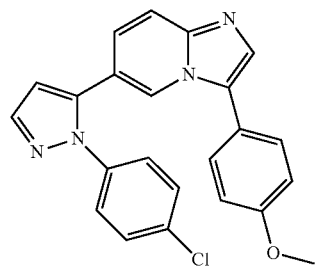 [SMILES: COc1ccc(-c2cnc3ccc(-c4ccnn4-c4ccc(Cl)cc4)cn23)cc1]

The title compound, white solid (41 mg, 31%), MS (ISP) m/z=401.6 [(M+H)$^+$], mp 142° C., was prepared in accordance with the general method of example 1 from 6-bromo-3-(4-methoxy-phenyl)-imidazo[1,2-a]pyridine (intermediate L) (0.1 g, 0.33 mmol) and 1-(4-chloro-phenyl)-5-(4,4,5,5-tetramethyl-[1,3,2]dioxaborolan-2-yl)-1H-pyrazole (intermediate B) (0.12 g, 0.39 mmol).

EXAMPLE 13

6-[2-(4-Fluoro-phenyl)-2H-pyrazol-3-yl]-3-(4-methoxy-phenyl)-imidazo[1,2-a]pyridine

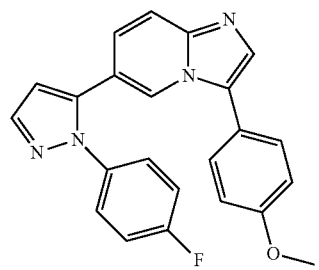

The title compound, white solid (56 mg, 44%), MS (ISP) m/z=385.5 [(M+H)$^+$], mp 162° C., was prepared in accordance with the general method of example 1 from 6-bromo-3-(4-methoxy-phenyl)-imidazo[1,2-a]pyridine (intermediate L) (0.1 g, 0.33 mmol) and 1-(4-fluoro-phenyl)-5-(4,4,5,5-tetramethyl-1,3,2-dioxaborolan-2-yl)-1H-pyrazole (intermediate A) (0.11 mg, 0.38 mmol).

EXAMPLE 14

3-(2,4-Difluoro-phenyl)-6-[2-(4-fluoro-phenyl)-2H-pyrazol-3-yl]-imidazo[1,2-a]pyridine

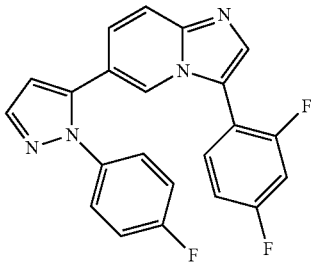 [SMILES: Fc1ccc(-n2nccc2-c2ccc3ncc(-c4ccc(F)cc4F)n3c2)cc1]

The title compound, white solid (56 mg, 44%), MS (ISP) m/z=391.5 [(M+H)+], mp 168° C., was prepared in accordance with the general method of example 1 from 6-bromo-3-(2,4-difluoro-phenyl)-imidazo[1,2-a]pyridine (intermediate K) (0.1 g, 0.324 mmol) and 1-(4-fluoro-phenyl)-5-(4,4,5,5-tetramethyl-1,3,2-dioxaborolan-2-yl)-1H-pyrazole (intermediate A) (0.11 mg, 0.38 mmol).

EXAMPLE 15

6-[2-(4-Chloro-phenyl)-2H-pyrazol-3-yl]-3-(2,4-difluoro-phenyl)-imidazo[1,2-a]pyridine

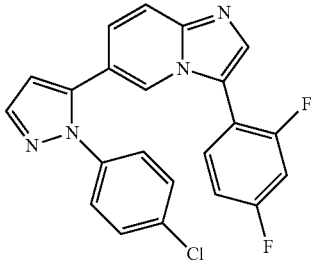 [SMILES: Fc1ccc(-c2cnc3ccc(-c4ccnn4-c4ccc(Cl)cc4)cn23)c(F)c1]

The title compound, white solid (40 mg, 30%), MS (ISP) m/z=407.4 [(M+H)+], mp 152° C., was prepared in accordance with the general method of example 1 from 6-bromo-3-(2,4-difluoro-phenyl)-imidazo[1,2-a]pyridine (intermediate K) (0.1 g, 0.324 mmol) and 1-(4-chloro-phenyl)-5-(4,4,5,5-tetramethyl-[1,3,2]dioxaborolan-2-yl)-1H-pyrazole (intermediate B) (0.12 g, 0.39 mmol).

EXAMPLE 16

3-(4-Fluoro-phenyl)-6-[3-(4-fluoro-phenyl)-3H-imidazol-4-yl]-imidazol[1,2-a]pyridine

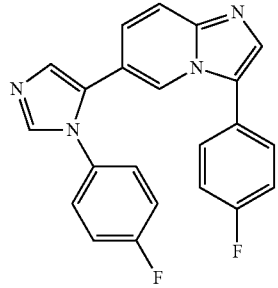 [SMILES: Fc1ccc(-c2cnc3ccc(-c4cncn4-c4ccc(F)cc4)cn23)cc1]

To a flame-dried reaction flask were added at room temperature and under an argon atmosphere commercially available 1-(4-fluorophenyl)-1H-imidazole (69.6 mg, 429 μmol), palladium(II)acetate (9.64 mg, 42.9 μmol), cesium fluoride (130 mg, 859 μmol), triphenylarsine (26.3 mg, 85.9 μmol) and 6-bromo-3-(4-fluoro-phenyl)-imidazo[1,2-a]pyridine (intermediate E) (125 mg, 429 μmol). Afterwards DMF (2.15 ml) was added successively by syringe at room temperature and under a stream of argon. The resulting mixture was allowed to stir at 140° C. under an argon atmosphere for 24 h. The reaction mixture was cooled to room temperature, water (10 ml) was added and the mixture was extracted with dichloromethane (2×40 ml). The combined organic layers were washed with water (2×20 ml), dried (MgSO4) and evaporated. The crude product was purified by flash chromatography on silica gel (dichloromethane/MeOH, 2-8%) and crystallization (dichloromethane/heptane) to yield the title compound as an off-white solid (50 mg, 31%), MS (ISP) m/z=373.4 [(M+H)+], mp 206° C.

EXAMPLE 17

6-[2-(4-Chloro-phenyl)-2H-pyrazol-3-yl]-3-(4-trifluoromethyl-phenyl)-imidazo[1,2-a]pyridine

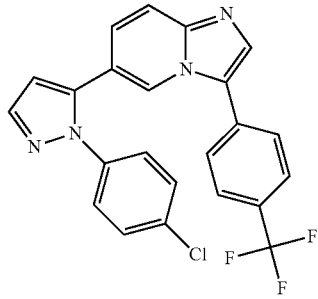

The title compound, off-white solid (72 mg, 56%), MS (ISP) m/z=439.5 [(M+H)+], mp 167° C., was prepared in accordance with the general method of example 1 from 6-bromo-3-(4-trifluoromethyl-phenyl)-imidazo[1,2-a]pyridine (intermediate M) (0.1 g, 0.29 mmol) and 1-(4-chloro-phenyl)-5-(4,4,5,5-tetramethyl-[1,3,2]dioxaborolan-2-yl)-1H-pyrazole (intermediate B) (0.12 g, 0.38 mmol).

EXAMPLE 18

6-[2-(4-Fluoro-phenyl)-2H-pyrazol-3-yl]-3-(4-trifluoromethyl-phenyl)-imidazo[1,2-a]pyridine

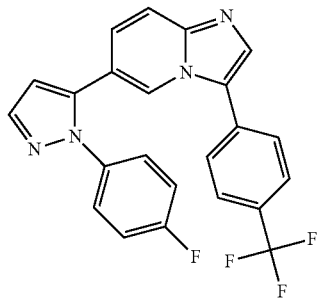 [SMILES: Fc1ccc(-n2nccc2-c2ccc3ncc(-c4ccc(C(F)(F)F)cc4)n3c2)cc1]

The title compound, off-white solid (87 mg, 70%), MS (ISP) m/z=423.5 [(M+H)+], mp 172° C., was prepared in accordance with the general method of example 1 from 6-bromo-3-(4-trifluoromethyl-phenyl)-imidazo[1,2-a]pyridine (intermediate M) (0.1 g, 0.29 mmol) and 1-(4-fluoro-phenyl)-5-(4,4,5,5-tetramethyl-1,3,2-dioxaborolan-2-yl)-1H-pyrazole (intermediate A) (0.11 mg, 0.38 mmol).

EXAMPLE 19

4-{6-[2-(4-Fluoro-phenyl)-2H-pyrazol-3-yl]-imidazo[1,2-a]pyridin-3-yl}-benzonitrile

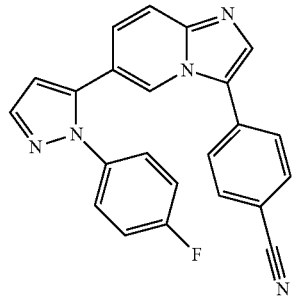 [SMILES: N#Cc1ccc(-c2cnc3ccc(-c4ccnn4-c4ccc(F)cc4)cn23)cc1]

The title compound, white solid (88 mg, 69%), MS (ISP) m/z=380.5 [(M+H)⁺], mp 215° C., was prepared in accordance with the general method of example 1 from 4-(6-bromo-imidazo[1,2-a]pyridin-3-yl)-benzonitrile (intermediate N) (0.1 g, 0.335 mmol) and 1-(4-fluoro-phenyl)-5-(4,4,5,5-tetramethyl-1,3,2-dioxaborolan-2-yl)-1H-pyrazole (intermediate A) (0.13 mg, 0.44 mmol).

EXAMPLE 20

4-{6-[2-(4-Chloro-phenyl)-2H-pyrazol-3-yl]-imidazo[1,2-a]pyridin-3-yl}-benzonitrile

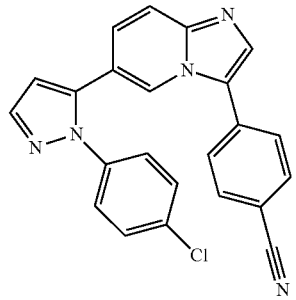

The title compound, white solid (78 mg, 59%), MS (ISP) m/z=396.5 [(M+H)⁺], mp 208° C., was prepared in accordance with the general method of example 1 from 4-(6-bromo-imidazo[1,2-a]pyridin-3-yl)-benzonitrile (intermediate N) (0.1 g, 0.335 mmol) and 1-(4-chloro-phenyl)-5-(4,4,5,5-tetramethyl-[1,3,2]dioxaborolan-2-yl)-1H-pyrazole (intermediate B) (0.13 g, 0.44 mmol).

EXAMPLE 21

6-[2-(4-Chloro-phenyl)-2H-pyrazol-3-yl]-3-(4-methanesulfonyl-phenyl)-imidazo[1,2-a]pyridine

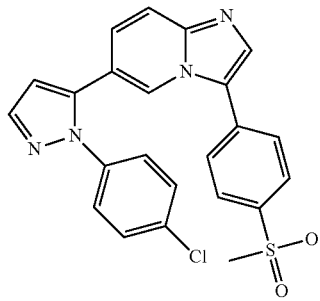

The title compound, white solid (84 mg, 66%), MS (ISP) m/z=449.6 [(M+H)⁺], mp 259° C., was prepared in accordance with the general method of example 1 from 6-bromo-3-(4-methanesulfonyl-phenyl)-imidazo[1,2-a]pyridine (intermediate O) (0.1 g, 0.285 mmol) and 1-(4-chloro-phenyl)-5-(4,4,5,5-tetramethyl-[1,3,2]dioxaborolan-2-yl)-1H-pyrazole (intermediate B) (0.11 g, 0.37 mmol).

EXAMPLE 22

6-[2-(4-Fluoro-phenyl)-2H-pyrazol-3-yl]-3-(4-methanesulfonyl-phenyl)-imidazo[1,2-a]pyridine

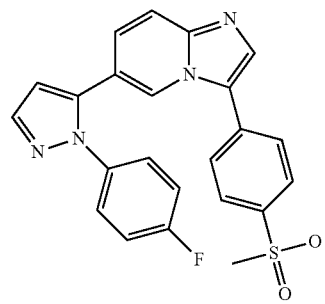

The title compound, white solid (79 mg, 64%), MS (ISP) m/z=433.6 [(M+H)⁺], mp 226° C., was prepared in accordance with the general method of example 1 from 6-bromo-3-(4-methanesulfonyl-phenyl)-imidazo[1,2-a]pyridine (intermediate O) (0.1 g, 0.285 mmol) and 1-(4-fluoro-phenyl)-5-(4,4,5,5-tetramethyl-1,3,2-dioxaborolan-2-yl)-1H-pyrazole (intermediate A) (0.11 mg, 0.37 mmol).

EXAMPLE 23

3-(4-Fluoro-phenyl)-6-[2-(4-trifluoromethyl-phenyl)-2H-pyrazol-3-yl]-imidazo[1,2-a]pyridine

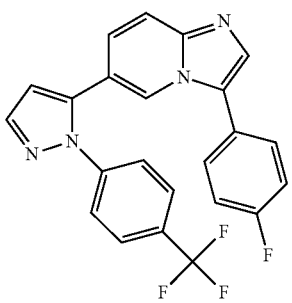 [SMILES: Fc1ccc(-c2cnc3ccc(-c4ccnn4-c4ccc(C(F)(F)F)cc4)cn23)cc1]

The title compound, white solid (37 mg, 26%), MS (ISP) m/z=423.6 [(M+H)⁺], mp 147° C., was prepared in accordance with the general method of example 1 from 6-bromo-3-(4-fluoro-phenyl)-imidazo[1,2-a]pyridine (intermediate E) (0.1 mg, 0.34 mmol) and 5-(4,4,5,5-tetramethyl-[1,3,2]dioxaborolan-2-yl)-1-(4-trifluoromethyl-phenyl)-1H-pyrazole (intermediate P) (0.15 g, 0.45 mmol).

EXAMPLE 24

4-{6-[2-(4-Trifluoromethyl-phenyl)-2H-pyrazol-3-yl]-imidazo[1,2-a]pyridin-3-yl}-benzonitrile

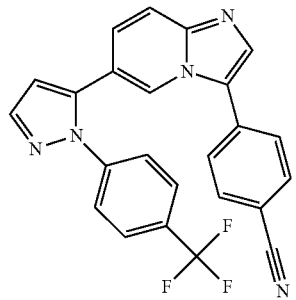 [SMILES: N#Cc1ccc(-c2cnc3ccc(-c4ccnn4-c4ccc(C(F)(F)F)cc4)cn23)cc1]

The title compound, off-white solid (59 mg, 41%), MS (ISP) m/z=430.6 [(M+H)+], mp 201° C., was prepared in accordance with the general method of example 1 from 4-(6-bromo-imidazo[1,2-a]pyridin-3-yl)-benzonitrile (intermediate N) (0.1 g, 0.335 mmol) and 5-(4,4,5,5-tetramethyl-[1,3,2]dioxaborolan-2-yl)-1-(4-trifluoromethyl-phenyl)-1H-pyrazole (intermediate P) (0.15 g, 0.44 mmol).

The invention claimed is:

1. A compound of formula I

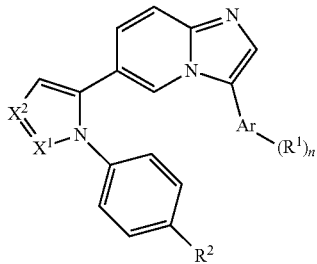

wherein

Ar is phenyl or pyridinyl;

$X^1$ is N or CH, $X^2$ is N or CH, with the proviso that only one of $X^1$ or $X^2$ is N and the other is CH;

$R^1$ is hydrogen, halogen, lower alkyl, lower alkoxy, lower alkyl substituted by halogen, cyano or $S(O)_2$-lower alkyl;

$R^2$ is hydrogen, halogen, lower alkyl, lower alkoxy, lower alkyl substituted by halogen or cyano;

n is 1 or 2;

or a pharmaceutically acceptable acid addition salt, a racemic mixture or its corresponding enantiomer and/or optical isomers thereof.

2. The compound of formula IA-1 according to claim 1,

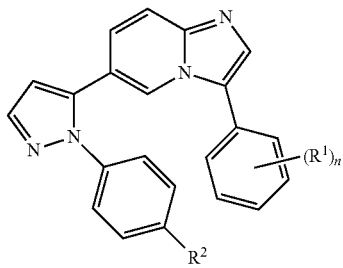

wherein $R^1$ is hydrogen, halogen, lower alkyl, lower alkoxy, lower alkyl substituted by halogen, cyano or $S(O)_2$-lower alkyl;

$R^2$ is hydrogen, halogen, lower alkyl, lower alkoxy, lower alkyl substituted by halogen or cyano;

n is 1 or 2;

or a pharmaceutically acceptable acid addition salt, a racemic mixture or its corresponding enantiomer and/or optical isomers thereof.

3. The compound of formula IA-1 according to claim 1, wherein the compound is selected from:
   3-(4-Fluoro-phenyl)-6-[2-(4-fluoro-phenyl)-2H-pyrazol-3-yl]-imidazo[1,2-a]pyridine
   3-(4-Chloro-phenyl)-6-[2-(4-chloro-phenyl)-2H-pyrazol-3-yl]-imidazo[1,2-a]pyridine
   6-[2-(4-Chloro-phenyl)-2H-pyrazol-3-yl]-3-(4-fluoro-phenyl)-imidazo[1,2-a]pyridine
   3-(4-Chloro-phenyl)-6-[2-(4-fluoro-phenyl)-2H-pyrazol-3-yl]-imidazo[1,2-a]pyridine
   3-(4-Fluoro-phenyl)-6-(2-p-tolyl-2H-pyrazol-3-yl)-imidazo[1,2a]pyridine
   3-Phenyl-6-(2-phenyl-2H-pyrazol-3-yl)-imidazo[1,2-a]pyridine
   3-(4-Chloro-2-fluoro-phenyl)-6-[2-(4-fluoro-phenyl)-2H-pyrazol-3-yl]-imidazo[1,2-a]pyridine
   3-Phenyl-6-(2-p-tolyl-2H-pyrazol-3-yl)-imidazo[1,2-a]pyridine
   3-(4-Chloro-2-fluoro-phenyl)-6-[2-(4-chloro-phenyl)-2H-pyrazol-3-yl]-imidazo[1,2-a]pyridine
   6-[2-(4-Chloro-phenyl)-2H-pyrazol-3-yl]-3-(4-methoxy-phenyl)-imidazo[1,2-a]pyridine
   6-[2-(4-Fluoro-phenyl)-2H-pyrazol-3-yl]-3-(4-methoxy-phenyl)-imidazo[1,2-a]pyridine
   3-(2,4-Difluoro-phenyl)-6-[2-(4-fluoro-phenyl)-2H-pyrazol-3-yl]-imidazo[1,2-a]pyridine
   6-[2-(4-Chloro-phenyl)-2H-pyrazol-3-yl]-3-(2,4-difluoro-phenyl)-imidazo[1,2-a]pyridine
   6-[2-(4-Chloro-phenyl)-2H-pyrazol-3-yl]-3-(4-trifluoromethyl-phenyl)-imidazo[1,2-a]pyridine
   6-[2-(4-Fluoro-phenyl)-2H-pyrazol-3-yl]-3-(4-trifluoromethyl-phenyl)-imidazo[1,2-a]pyridine
   4-{6-[2-(4-Fluoro-phenyl)-2H-pyrazol-3-yl]-imidazo[1,2-a]pyridin-3-yl}-benzonitrile
   4-{6-[2-(4-Chloro-phenyl)-2H-pyrazol-3-yl]-imidazo[1,2-a]pyridin-3-yl}-benzonitrile
   6-[2-(4-Chloro-phenyl)-2H-pyrazol-3-yl]-3-(4-methanesulfonyl-phenyl)-imidazo[1,2-a]pyridine
   6-[2-(4-Fluoro-phenyl)-2H-pyrazol-3-yl]-3-(4-methanesulfonyl-phenyl)-imidazo[1,2-a]pyridine 3-(4-Fluoro-phenyl)-6-[2-(4-trifluoromethyl-phenyl)-2H-pyrazol-3-yl]-imidazo[1,2-a]pyridine or 4-{6-[2-(4-Trifluoromethyl-phenyl)-2H-pyrazol-3-yl]-imidazo[1,2-a]pyridin-3-yl}-benzonitrile.

4. The compound of formula IA-2 according to claim 1,

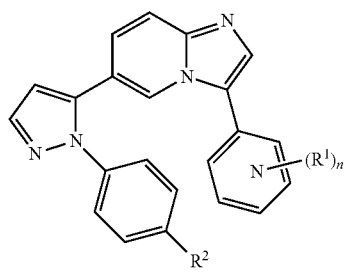

wherein

⬡ is a pyridine group, wherein the N-atom may be in 2, 3 or 4 position;

R¹ is hydrogen, halogen, lower alkyl, lower alkoxy, lower alkyl substituted by halogen, cyano or S(O)₂-lower alkyl;

R² is hydrogen, halogen, lower alkyl, lower alkoxy, lower alkyl substituted by halogen or cyano;

n is 1 or 2;

or a pharmaceutically acceptable acid addition salt, a racemic mixture or its corresponding enantiomer and/or optical isomers thereof.

5. The compound of formula IA-2 according to claim 1, wherein the compound is selected from:

6-[2-(4-Fluoro-phenyl)-2H-pyrazol-3-yl]-3-pyridin-4-yl-imidazo[1,2-a]pyridine or 6-[2-(4-Chloro-phenyl)-2H-pyrazol-3-yl]-3-pyridin-4-yl-imidazo[1,2-a]pyridine.

6. The compound of formula B according to claim 1,

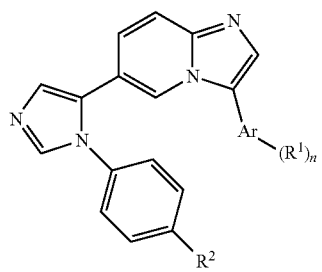

wherein

Ar is phenyl or pyridinyl;

R¹ is hydrogen, halogen, lower alkyl, lower alkoxy, lower alkyl substituted by halogen, cyano or S(O)₂-lower alkyl;

R² is hydrogen, halogen, lower alkyl, lower alkoxy, lower alkyl substituted by halogen or cyano;

n is 1 or 2;

or a pharmaceutically acceptable acid addition salt, a racemic mixture or its corresponding enantiomer and/or optical isomers thereof.

7. The compound of formula IB according to claim 1, which compound is 3-(4-Fluoro-phenyl)-6-[3-(4-fluoro-phenyl)-3H-imidazol-4-yl]-imidazo[1,2-a]pyridine.

8. A process for the manufacture of a compound of formula I as defined in claim 1, which process comprises a) reacting a compound of formula

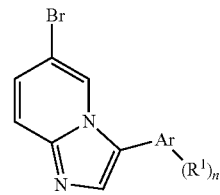

with a compound of formula

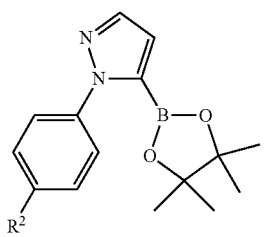

to a compound of formula

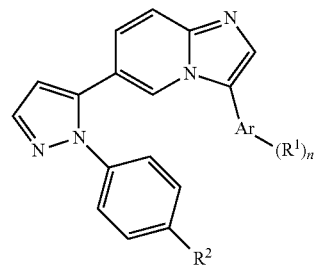

and, if desired, converting the compounds obtained into pharmaceutically acceptable acid addition salts.

b) reacting a compound of formula

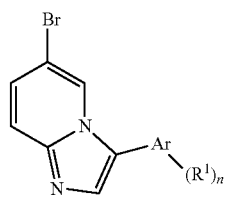

with a compound of formula

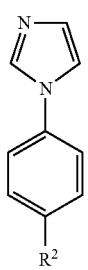

to a compound of formula
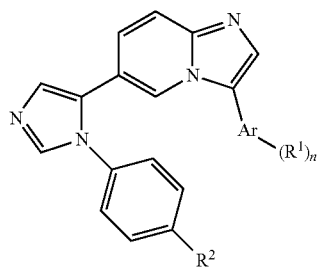
IB
and, if desired, converting the compounds obtained into pharmaceutically acceptable acid addition salts.
9. A compound according to claim 1 when manufactures by a process according to claim 8.
10. A pharmaceutical composition comprising a compound according to claim 1 and a pharmaceutical acceptable carrier and/or adjuvant.
* * * * *